United States Patent [19]

Wolf et al.

[11] Patent Number: 4,829,061

[45] Date of Patent: May 9, 1989

[54] 1-(4-HYDROXY-3,5-DI-TERT.-BUTYLBEN-ZOYL)HOMOPIPERAZINE, VARIOUS DERIVATIVES THEREOF, PROCESSES FOR THE PREPARATION OF THESE COMPOUNDS, MEDICAMENTS CONTAINING THEM, AND THEIR USE

[75] Inventors: Erhard Wolf, Hofheim am Taunus; Erhard Rossmanith, Schwalbach/Taunus; Robert R. Bartlett, Darmstadt; Rudolf Schleyerbach, Hofheim am Taunus, all of Fed. Rep. of Germany

[73] Assignee: Hoechst Aktiengesellschaft, Frankfurt am Main, Fed. Rep. of Germany

[21] Appl. No.: 149,602

[22] Filed: Jan. 28, 1988

[30] Foreign Application Priority Data

Jan. 30, 1987 [DE] Fed. Rep. of Germany ....... 3702755

[51] Int. Cl.$^4$ .................. C07D 243/08; A61K 31/55
[52] U.S. Cl. ..................................... 514/218; 540/575
[58] Field of Search ......................... 540/575; 514/218

[56] References Cited

U.S. PATENT DOCUMENTS 4,066,614 1/1978 Oppelt et al. ..................... 260/45.8

4,404,302 9/1983 Gupta et al. ........................ 524/100

FOREIGN PATENT DOCUMENTS 190685 8/1986 European Pat. Off. ............ 544/391

OTHER PUBLICATIONS

European Search Report.
T. Takahashi et al., Chem. Abstr., vol. 77, No. 7, 48520m (1972).
T. Takahashi et al., Chem. Abstr., vol. 75, No. 5, 36162s (1971).
K. Brune, Eur. J. Rheumatol. Inflam., 5, 1982, pp. 335–349.

Primary Examiner—Robert Gerstl
Attorney, Agent, or Firm—Finnegan, Henderson, Farabow, Garrett, & Dunner

[57] ABSTRACT 1-(4-Hydroxy-3,5-di-tert.-butylbenzoyl)homopiperazine and various derivatives thereof substituted on the nitrogen are prepared starting from 4-hydroxy-3,5-di-tert.-butylbenzoic acid or its derivatives and homopiperazine or appropriate derivatives thereof.

The compounds and their physiologically tolerated acid addition salts are suitable for the treatment of inflammatory and painful, in particular inflammatory rheumatic, disorders.

9 Claims, No Drawings

1-(4-HYDROXY-3,5-DI-TERT.-BUTYLBENZOYL)-HOMOPIPERAZINE, VARIOUS DERIVATIVES THEREOF, PROCESSES FOR THE PREPARATION OF THESE COMPOUNDS, MEDICAMENTS CONTAINING THEM, AND THEIR USE

The present invention relates to 1-(4-hydroxy-3,5-di-tert.-butylbenzoyl)homopiperazine, various derivatives thereof, processes for the preparation of these compounds and their use as active ingredients in medicaments, mainly for the treatment of rheumatic disorders, in particular the forms which have a severe course, such as chronic graft-versus-host diseases which it has hitherto been hardly possible to treat, and of autoimmune diseases mediated by immune complexes, such as, for example, systemic lupus erythematosus, immune complex glomerulonephritis and type I diabetes.

The substances which are preferably used for the treatment of rheumatic disorders are non-steroidal antirheumatics (=NSAID) which are preferably recruited from the classes of aralkylcarboxylic acids, anthranilic acid, oxicams, salicylic acid and pyrazoles. Although these antirheumatics are able to have beneficial effects on the pain associated with the disease, and the inflammation and swelling, they may lead to serious side effects (cf. K. Brune, Eur. J. Rheumatol. Inflam. 5 (1982), pages 335–349; Litera Rheumatologica 3, Symposium report, F. J. Wagenhäuser, Nutzen und Risiken der Antirheumatika (Benefits and Risks of the Antirheumatics), Basle, 1985): apart from renal function disturbances and allergic reactions, such as attacks of asthma, there are observed to be, in particular, gastrointestinal disturbances, and it appears that the chemical structure of the NSAIDs which are used is of minor importance (Coles, L.S. et al Amer. J Med. 74, 1983, page 820). A further disadvantage is the often narrow therapeutic range of these compounds.

Moreover, treatment of the forms with a severe course is scarcely possible with NSAIDs, or is possible only by accepting serious side effects when immunosuppressants are used, such as, for example, cyclophosphamide, cyclosporin A, methotrexate or glucocorticoids. The latter may lead to, inter alia, nausea, stomatitis, changes in the blood picture and hepato- or nephrotoxicity.

It has now been found, surprisingly, that 1-(4-hydroxy-3,5-di-tert.-butylbenzoyl)homopiperazine and various derivatives thereof substituted on the nitrogen are able to have beneficial effects on the chronic graft-versus-host diseases which it has hitherto been hardly possible to treat, and the autoimmune diseases mediated by immune complexes, while the tolerability is very good, the therapeutic range is advantageous, and the antiinflammatory property is retained. In contrast to this, the 3,5-di-tert.-butyl-4-hydroxybenzamides disclosed in U.S. Pat. No. 4,128,664 only have antiinflammatory activity, and thus are not suitable for the treatment of the said severe disorders.

The present invention relates to 1-(4-hydroxy-3,5-di-tert.- butylbenzoyl)homopiperazine and derivatives thereof substituted on the nitrogen, of the following general formula I

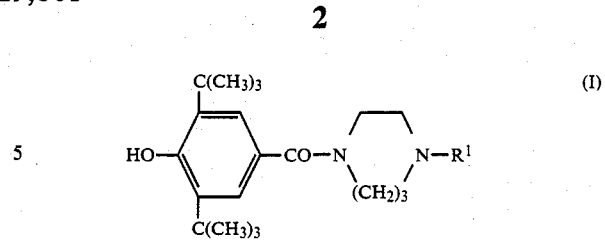

in which $R^1$ represents H, a straight-chain or branched $(C_1–C_6)$-alkoxycarbonyl radical ($CH_3OCO$, $C_2H_5OCO$, tert.-$C_4H_9OCO$, etc.) or the benzyloxycarbonyl radical, which can be substituted in the phenyl radical, and their physiologically tolerated salts. Examples of suitable substituents on the phenyl nucleus in the benzyloxycarbonyl radical are:

halogen (F, Cl, Br, I, preferably Cl), $(C_1–C_4)$-alkyl, $(C_1–C_4)$-alkoxy, halogenoalkyl (preferably having 1–3 carbon atoms, such as $CF_3$, $C_2H_4Cl$, etc.), etc.

The compounds of the formula I which are preferred are those in which $R^1$ is H, a straight-chain or branched $(C_1–C_4)$-alkoxycarbonyl radical or the benzyloxycarbonyl radical (unsubstituted in the phenyl radical); $R^1$ is particularly preferably only H or the benzyloxycarbonyl radical (unsubstituted in the phenyl radical).

The compounds of the formula I are advantageously prepared by reaction of 3,5-di-tert.-butyl-4-hydroxybenzoic acid and its derivatives of the formula II

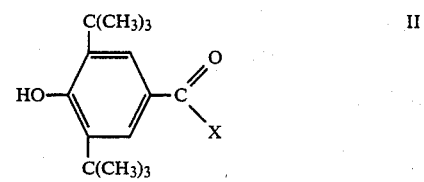

in which X=
OH
halogen (F, Cl, Br or I),
$N_3$
Oalkyl (preferably $OC_1–C_4$-alkyl)
Oaryl (preferably $OC_6H_5$)

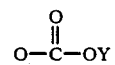

(with Y=alkyl, aryl, aralkyl, preferably $C_1–C_4$-alkyl, $C_6H_5$, $CH_2C_6H_5$) or

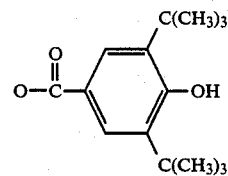

with amines of the formula III

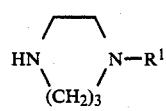

in which $R^1$ has the same meaning as in formula I.

The particularly preferred starting compound of the formula II is 3,5-di-tert.-butyl-4-hydroxybenzoyl chloride.

3,5-Di-tert.-butyl-4-hydroxybenzoic acid itself can be obtained in a known manner, for example using Kolbe's synthesis from the corresponding phenol (2,6-di-tert.-butylphenol) and $CO_2$, by a Cannizzaro reaction or by oxidative means, for example from the corresponding aldehyde or the methyl compound. The appropriate derivatives of the formula II can be obtained from the acid by customary processes. 2,6-Di-tert.-butylphenol is a commercially available product.

Examples of suitable starting amines of the formula III are: homopiperazine, N-ethoxycarbonylhomopiperazine, N-tert.-butyloxycarbonyl- and N-benzyloxycarbonyl-homopiperazine.

Where starting compounds of the formula II with X=OH, halogen, $N_3$, Oalkyl, Oaryl or OC(O)OY are used, these compounds and the amines of the formula III are preferably used in a molar ratio of 1: at least about 1; where 3,5-di-tert.-butylbenzoic anhydride is used as starting compound of the formula II, the molar ratio to the amine III is preferably 1: at least about 2.

The reaction can be carried out without solvent. However, it is preferably carried out with the addition of an inert dispersant or solvent such as, for example, an aliphatic amide (dimethylformamide, dimethylacetamide etc.), nitrile (acetonitrile etc.), ether (diethyl or diisopropyl ether, tetrahydrofuran, dioxane, glycol diethyl ether, diethylene glycol dimethyl ether etc.) or alcohol (methanol, ethanol, propanol, isopropanol etc.). It may also be advantageous to increase the rate of reaction by, for example, addition of a base or by catalytic amounts of dimethylformamide etc. When the acid halides—in particular the acid chloride—are used as starting compounds of the formula II, it is advantageous to carry out the reaction in the presence of acid-binding agents, such as alkali metal and alkaline earth metal carbonates, hydroxides or alcoholates, organic bases (triethylamine, pyridine, picoline, quinoline etc.) or the amine of the formula III which is used in excess.

The reaction temperatures are expediently between about 0° and 160° C., preferably between about 20° and 80° C.

When the amides of the formula I are prepared from esters, it may prove beneficial, where appropriate, to use activated esters such as, for example, cyanomethyl or carboxymethyl esters. If the free carboxylic acid (compound of the formula II with X=OH) is reacted to give the compounds of the formula I according to the invention, it is advisable to use water-binding reagents such as, for example, dicyclohexylcarbodiimide.

It may be advantageous for the preparation of the compound of the formula I, according to the invention, with a free NH group (=1-(4-hydroxy-3,5-di-tert.-butylbenzoyl)homopiperazine) to protect the NH group with a radical which can readily be eliminated, for example with the carbobenzoxy group or another—activated where possible—ester or acyl group, and to eliminate the latter after the reaction with a compound of the formula II, with liberation (by hydrogenolysis or hydrolysis) of the NH group.

It is advantageous, especially when the compound of the formula I contains the free basic NH group, to isolate the final product as a salt of physiologically tolerated acids. Examples of suitable salts for therapeutic use are the hydrochloride, the neutral or acidic sulfate, the primary, secondary or tertiary phosphate, the methane- or p-toluenesulfonate or the salt of an organic acid such as, for example, the maleate or citrate. It is particularly advantageous to use the water-soluble hydrochloride, which is prepared by known processes—for example by reaction of the basic compound I in alcoholic solution or suspension with, preferably, the equivalent amount of alcoholic or aqueous hydrochloric acid.

The compounds of the formula I, according to the invention, and the corresponding physiologically tolerated acid addition salts are suitable for use as medicines or as active ingredients in medicines. They display anti-inflammatory effects, but are particularly distinguished by being suitable for the treatment of chronic graft-versus-host diseases and of autoimmune diseases mediated by immune complexes, and having a favorable therapeutic range. Furthermore, they are very well tolerated.

The appropriate medicaments contain—or comprise at least one compound of the formula I and/or at least one of its physiologically tolerated acid addition salts; they are mainly used for the prevention and treatment of rheumatic disorders, preferably for the forms having a severe course.

The medicaments are prepared by converting at least one compound of the formula I, and/or at least one physiologically tolerated acid addition salt of such a compound, and/or at least one of the compounds obtained by the process described above, into a suitable dosage form with a physiologically tolerated vehicle and, where appropriate, further additives and/or auxiliaries.

Particularly suitable presentations are tablets, coated tablets, capsules and suppositories; they can contain the active ingredients either in the free form (compounds of the formula I) or in the form of the appropriate physiologically tolerated acid addition salts. Particularly used for intravenous administration are aqueous solutions of the salts, which may, where appropriate, also contain solubilizers.

All these formulations can also contain other therapeutically active components such as, for example, analgesics.

The examples which follow are intended to explain the invention further.

EXAMPLE 1

1-(4-Hydroxy-3,5-di-tert.-butylbenzoyl)-4-benzyloxycarbonylhomopiperazine

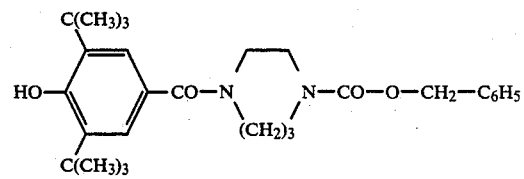

A mixture of 13.4 g (0.05 mol) of 3,5-di-tert.-butyl-4-hydroxybenzoyl chloride and 12.4 g (0.053 mol) of 1-benzyloxycarbonylhomopiperazine in 200 ml of acetonitrile is heated under reflux, with stirring, for 6 hour. The solvent is then removed by distillation under reduced pressure, the residue is partitioned between methylene chloride and dilute hydrochloric acid, and the organic phase is separated off and washed with saturated brine. After drying over sodium sulfate and removal of the solvent by distillation under reduced pressure, the crystalline residue is digested with hot diisopropyl ether, filtered off with suction, washed with diisopropyl ether and dried.

Yield: 16 g (69% of theory)
Melting point: 146° C.
$C_{28}H_{38}N_2O_4$ (MW=466.6)
Analysis: Calculated: C 72.07%, H 8.21%, N 6.00%, Found: C 71.76%, H 8.31%, N 5.97%.

EXAMPLE 2

1-(4-Hydroxy-3,5-di-tert.-butylbenzoyl)homopiperazine

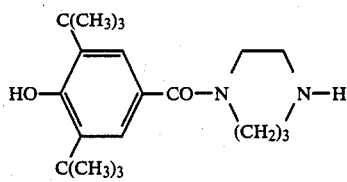

A mixture of 46.6 g (0.1 mol) of 1-(4-hydroxy-3,5-di-tert.-butylbenzoyl)-4-benzyloxycarbonylhomopiperazine (Example 1), 350 ml of glacial acetic acid and 2.3 g of palladium black is treated with hydrogen while stirring at 70°–80° C. for about 7 hours. The catalyst is then filtered off, and the solvent is removed by distillation under reduced pressure. The residue is dissolved in methylene chloride, and the solution is extracted by shaking with dilute sodium hydroxide solution and separated off. The organic phase is washed several times with water and then dried over anhydrous sodium sulfate. The residue left after the solvent has been removed in vacuo is recrystallized from acetonitrile with the addition of active charcoal.

Yield: 25 g (75% of theory)
Melting point: 124° C.
$C_{20}H_{32}N_2O_2$ (MW=332.5)
Analysis: Calculated: C 72.25%, H 9.7%, N 8.43%, Found: C 72.10%, H 9.58%, N 8.52%.

Pharmacological test and results

The antiinflammatory effect of the compounds of the formula I, according to the invention, was tested on adjuvant arthritis, and the effect on forms of rheumatic disorders having a severe course (chronic graft-versus-host diseases and autoimmune diseases mediated by immune complexes) was tested on the chronic graft-versus-host (cGvH) reaction in the mouse and in the reverse passive Arthus reaction in the rat in accordance with the animal models described below. The tolerability was determined by determining the toxicity in rats, namely by continuous administration for 14 days.

1. Adjuvant arthritis

The investigations were carried out by the method of Pearson (Arthrit. Rheum. 2 (1959) page 44). The test animals used were male rats of a Wistar-Lewis strain with a body weight between 130 and 200 g. The compounds to be tested were administered orally (p.o.) in doses of 50 mg per kg of body weight once a day from the 1st to the 5th day of the experiment. The animals in a control group received only the vehicle. Each product and control group comprised 8 animals. The criterion used for an effect was the percentage reduction in the increase in paw volume compared with that in the untreated control group.

| Compound from Example | Dose (mg/kg p.o.) | % inhibition in paw volume day 5 |
|---|---|---|
| 1 | 50 | 25 |
| 2 | 50 | 34 |

The substances significantly inhibit the adjuvant-induced arthritis in the rat.

2. Chronic graft-versus-host (cGvH) reaction in the mouse

The features of graft-versus-host disease, which is based on an immune reaction originating from the transplant and directed against the host tissue, are, in the form having an acute course which almost always ends fatally, enlargement of the spleen, hepatomegaly, lymph node hypertrophy, hemolytic anemia, low immunoglobulin and complement levels, and diminished immunoreactivity. The chronic form of the disease, which has a somewhat milder course, results in lymphadenopathy, immune complex glomerulonephritis and excessive formation of non-organ-specific autoantibodies. The clinical picture of systemic lupus erythematosus (SLE), which is likewise one of the autoimmune diseases, has similar features.

Investigation of the compounds used according to the invention on the course of the cGvH disease induced in response to two injections of spleen and thymus cells, mixed together, in female mice of the (DBA/2×C57Bl/6)F1 generation was carried out by the design of experiment described by S. Popovic and R. R. Bartlett (Agents and Actions 21 (1987), 284–286), with intravenous administration, at a time interval of 7 days, of, in each case, $5 \times 10^7$ DBA/2 cells, likewise obtained from female donor animals, in 0.2 ml of culture medium. For reliable assessment of the course and appearance of the disease, a group of healthy animals was included as negative controls in all the experiments. The 6-week oral treatment of the animals with the disease took place from day 21 after the first donor cell injection, with administration once a day of the test substance or the pure vehicle (positive controls). The vehicle used was an aqueous solution of CMC (carboxymethylcellulose sodium salt) containing 100 mg of CMC per 1. The volume administered was 10 ml per kg of body weight. Each of the individual experimental groups comprised 10 animals.

The action of the product was assessed on the basis of the inhibition of proteinuria and the cGvH index. The animals with the disease develop, as a consequence of the damage to nephrons due to deposition of immune complexes on the basement membranes of the glomeruli, a pronounced proteinuria which correlates with the extent of the glomerulonephritis and can easily be quantified by the increase in the amount of protein excreted with the urine. The second measured parameter, the cGvH index, is based on the great enlargement of the spleen (splenomegaly) caused by the cGvH reaction. It is defined as the quotient of the product of the spleen and body weights of the animals with the disease and the product of the corresponding weights of healthy untreated animals from the negative control group, and is a reliable measure of the intensity of the disease (the larger this index, the greater the disease).

The results of these investigations, which are compiled in the table, demonstrate that compounds of the formula I are able to bring about long-lasting alleviation of cGvH disease by intervening to modulate the autoimmune processes. NSAIDs show no effect in this test.

| Compound from Example | Dose in mg/kg/day p.o. | % inhibition Proteinuria | cGvH index |
|---|---|---|---|
| 1 | 5 | 100 | 57 |
|  | 20 | 80 | 75 |

3. Reverse passive arthus reaction in the rat

The experimental animals used were female and male Sprague-Dawley rats with a body weight between 80 and 100 g. The rats were divided into groups each comprising 8 animals. 1 hour before the Arthus reaction was induced by injection of 0.1 ml of an anti-rat IgG solution (0.6 mg/ml) into the right rear paw, the particular test substance or the pure vehicle (positive controls) was administered orally. Sodium chloride solution was injected into the left paw. A group of non-sensitized animals (negative controls) was likewise treated with ovalbumin in order to be able to rule out non-specific reactions to the protein. The parameter used to measure the action of the products was the percentage change in the increase in paw volume compared with that in the control group (positive controls) which, although sensitized, was untreated, 4 hours after the ovalbumin challenge, when the swelling had reached its maximum.

| Compound from Example | Reverse passive Arthus reaction Dose in mg/kg p.o. | % inhibition |
|---|---|---|
| 1 | 100 | 25 |
| 2 | 20 | 28 |
|  | 25 | 37 |

4. Determinations of toxicity in the rat

Groups of 10 male and female Wistar rats were fed each day for a period of 14 days with 50 or 75 mg/kg p.o., and were weighed every 2 days. The experiment was terminated after 14 days, and the weight gain was determined. The same number of rats not treated with the products acted as controls. The compounds of Examples 1 and 2 caused no significant change in the weights. This is regarded as a critical parameter for the tolerability of a compound.

We claim:

1. 1-(4-Hydroxy-3,5-di-tert.-butylbenzoyl)homopiperazine and derivatives thereof substituted on the nitrogen, of the formula I

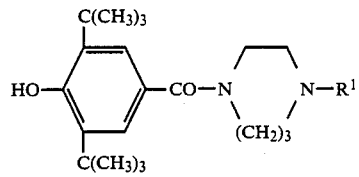

in which
R$^1$ represents a hydrogen atom, a straight-chain or branched (C$_1$-C$_6$)-alkyloxycarbonyl radical, the benzyloxycarbonyl radical or the benzyloxycarbonyl radical which is substituted in the phenyl nucleus by one or more of a halogen atom, a (C$_1$-C$_4$)-alkyl radical, a (C$_1$-C$_4$)-alkoxy radical or a (C$_1$-C$_3$)-halogenoalkyl radical,
and the physiologically tolerated acid addition salts thereof.

2. Compounds and their acid addition salts as claimed in claim 1, wherein in formula I the radical R$^1$ represents hydrogen atom or a straight-chain or branched (C$_1$-C$_6$)-alkyloxycarbonyl radical or the benzyloxycarbonyl radical.

3. Compounds and their acid addition salts as claimed in claim 1, wherein in formula I the radical R$^1$ represents a hydrogen atom or the benzyloxycarbonyl radical.

4. A pharmaceutical composition comprising an amount effective for use as a pharmaceutical in the prevention and treatment of inflammatory disorders of at least one of a compound of the formula I as claimed in claim 1 and a physiologically tolerated acid addition salt thereof.

5. A pharmaceutical composition as claimed in claim 4 for use in the prevention and treatment of rheumatic disorders.

6. A method for treating a patient suffering from an inflammatory disease which comprises administering to said patient a pharmaceutical composition as claimed in claim 4.

7. A method as claimed in claim 6 for treating a patient suffering from an inflammatory rheumatic disease.

8. A method for treating a patient suffering from an inflammatory disease which comprises administering to said patient an effective amount of at least one of a compound of the formula I as claimed in claim 1 and a physiologically tolerated acid addition salt thereof.

9. A method as claimed in claim 8 for treating a patient suffering from an inflammatory rheumatic disease.

* * * * *